(12) United States Patent
Oh et al.

(10) Patent No.: US 11,396,490 B2
(45) Date of Patent: Jul. 26, 2022

(54) METHOD FOR PREPARING CONTRAST AGENT IOMEPROL

(71) Applicant: UK CHEMIPHARM CO., LTD, Gyeonggi-do (KR)

(72) Inventors: Young-Seon Oh, Gyeonggi-do (KR); Jung-Jin Kim, Gyeonggi-do (KR); Young-Keun Lee, Gyeonggi-do (KR); Young-Nam Cha, Incheon (KR); Gi-Bum Oh, Seoul (KR)

(73) Assignee: UK CHEMIPHARM CO., LTD, Gyeonggi-do (KR)

( * ) Notice: Subject to any disclaimer, the term of this patent is extended or adjusted under 35 U.S.C. 154(b) by 0 days.

(21) Appl. No.: 17/276,864

(22) PCT Filed: Jul. 2, 2019

(86) PCT No.: PCT/KR2019/008008
§ 371 (c)(1),
(2) Date: Mar. 17, 2021

(87) PCT Pub. No.: WO2020/060010
PCT Pub. Date: Mar. 26, 2020

(65) Prior Publication Data
US 2022/0024857 A1  Jan. 27, 2022

(30) Foreign Application Priority Data
Sep. 17, 2018  (KR) .......... 10-2018-0110628

(51) Int. Cl.
*C07C 231/12* (2006.01)
*C07C 235/42* (2006.01)

(52) U.S. Cl.
CPC .......... *C07C 231/12* (2013.01); *C07C 235/42* (2013.01)

(58) Field of Classification Search
None
See application file for complete search history.

(56) References Cited

U.S. PATENT DOCUMENTS 4,352,788 A  10/1982  Felder et al.

FOREIGN PATENT DOCUMENTS

| CN | 102276498 | * | 10/2013 |
| CN | 107253918 | A | 10/2017 |
| KR | 10-2013-0090408 | A | 8/2013 |
| KR | 10-2015-0082293 | A | 7/2015 |
| KR | 10-2017-0123748 | A | 11/2017 |
| KR | 20170123748 | * | 11/2017 |
| KR | 10-1833334 | B1 | 2/2018 |
| WO | WO-8809328 | A1 | 12/1988 |
| WO | WO-003256 | A1 | 1/2000 |

OTHER PUBLICATIONS

International Search Report from corresponding PCT Application No. PCT/KR2019/008008, dated Oct. 8, 2019.

* cited by examiner

*Primary Examiner* — Amy C Bonaparte
(74) *Attorney, Agent, or Firm* — Harness, Dickey & Pierce, P.L.C.

(57) ABSTRACT

The present invention relates to a method for preparing an X-ray contrast agent iomeprol and, more specifically, to a method for preparing iomeprol by adding an inorganic base, an inorganic chloride, a solvent, etc. to 5-(2-hydroxyacetamido)-N,N'-bis(2,3-dihydroxypropyl)-2,4,6-triiodoisophthalamide (1b) to cause N-methylation reaction, thereby enabling easy separation and removal of inorganic salts generated during the reaction, without treatment with an ion exchange resin, while reducing the conventional production time, and minimization of the amount of reaction impurities.

11 Claims, No Drawings

METHOD FOR PREPARING CONTRAST AGENT IOMEPROL

CROSS-REFERENCE TO RELATED APPLICATIONS

This application is a national phase application of PCT Application No. PCT/KR2019/008008, filed on Jul. 2, 2019, which claims the benefit and priority to Korean Patent Application No. 10-2018-0110628, filed on Sep. 17, 2018. The entire disclosures of the applications identified in this paragraph are incorporated herein by references.

TECHNICAL FIELD

The present invention relates to a novel method for preparing an X-ray contrast agent iomeprol.

More specifically, the present invention relates to a novel method for preparing an X-ray contrast agent iomeprol which is capable of easily separating and removing inorganic salts generated during a reaction without treatment with an ion exchange resin while shortening the existing manufacturing time through a one-step synthesis process by performing N-methylation reaction by adding an inorganic base, an inorganic chloride and a solvent to 5-(2-hydroxyacetamido)-N,N'-bis(2,3-dihydroxypropyl)-2,4,6-triiodoisophthalamide.

The present invention can obtain iomeprol, a contrast agent compound, economically with a high purity of 99% or more through the one-step synthesis process and recrystallization as described above.

BACKGROUND ART

Iomeprol is a nonionic third-generation contrast agent which is N,N'-bis(2,3-dihydroxypropyl)-5-(2-hydroxy-N-methylacetamido)-2,4,6-triiodoisophthalamide having the structure of the following Formula 1a. It is prepared by methylating a compound of the following Formula 1 b. It is a triiodoisophthalamide X-ray and CT contrast agent developed by Bracco Imaging S.p.A, Italy, and is used in various applications of angiography, and was first described in European Patent No. EP0026281.

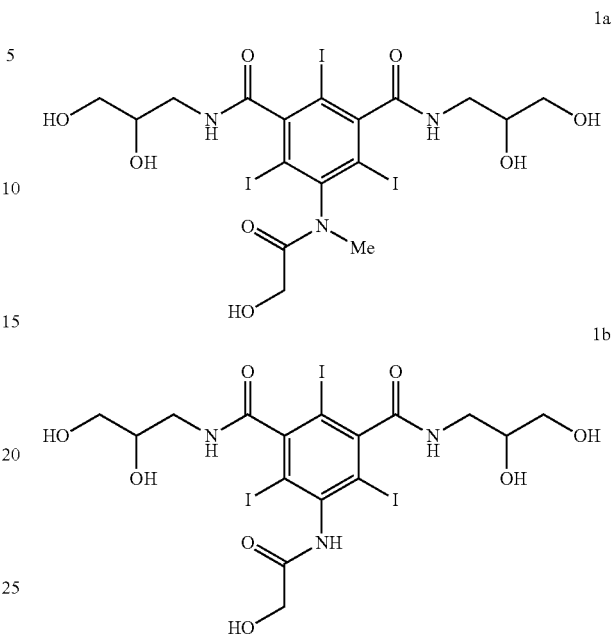

In addition, synthetic production routes for obtaining 5-(hydroxyacyl)amino derivatives based on the Smiles rearrangement reaction are described in International Publication Nos. WO88/09328 and WO00/32651.

The advantage of the synthesis method described in International Publication No. WO00/32561 is mainly that some reagents and solvents such as thionyl chloride, acetic anhydride, methyl iodide, methylene chloride and chloroform are not used, or avoidance of hydrogen reactions using catalysts, etc.

The synthesis process of the above contents is as follows (Scheme 1).

[Scheme 1]

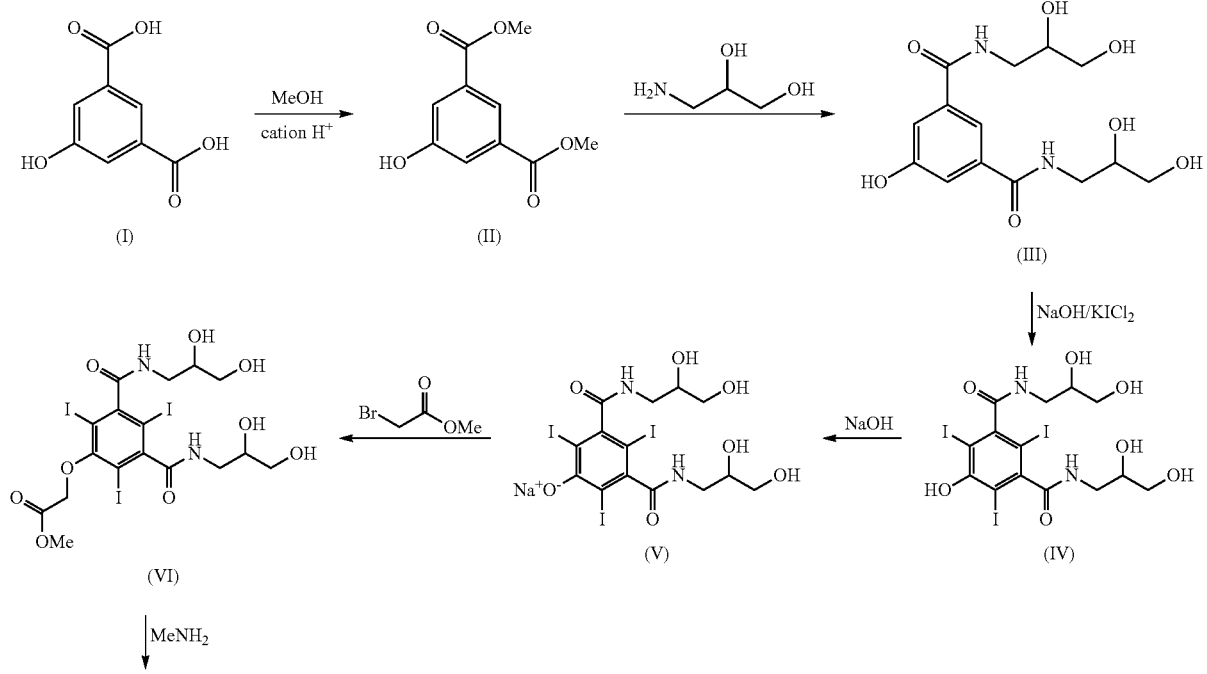

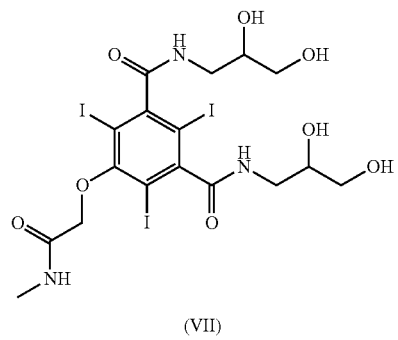

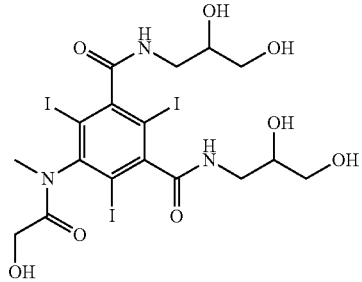

(VII)

The synthesis method of International Publication No. WO00/32561 does not use harmful substances under industrial production conditions. However, the synthesis step is long and has an alcohol group in the terminal group from the compound of Formula (III) to the compound of the last step, indicating water solubility. Thus, there is a difficult problem in removing the inorganic material used in steps 4 and 7.

Since iomeprol is soluble in water, it is very difficult to separate and remove if inorganic salts are generated during the manufacturing process.

In order to solve this problem and obtain a high-purity target product, not only iomeprol but also other iodine-based contrast agents are purified by using an ion exchange resin in the final step of removing inorganic substances.

In terms of industrial production conditions, the ion exchange resin device has an economical disadvantage in that the equipment cost is not small, requires an installation space and requires replacement of the resin within a certain period.

The synthesis method described in International Publication No. WO88/09328 has a shorter manufacturing process than that of International Publication No. WO00/32561. However, since inorganic salts are also used in the final stage of International Publication No. WO88/09328, an ion exchange resin device must be used to separate the produced iomeprol and inorganic substances.

A preparing method without ion exchange resin treatment, which was used for suppressing the formation of inorganic substances, which was a problem in the above patents, was registered as Korean Patent No. 101833334 by the present applicant.

In the above patent, each alcohol group of the starting material is acetylated to synthesize a protecting group so that it is well soluble in an organic solvent.

Subsequently, a method of synthesizing iomeprol from which inorganic substances have been removed through a deprotection reaction after methylation reaction of synthesized new material N,N'-bis(2,3-diacetylatepropyl)-5-(2-acetoxy-N-methylacetamido)-2,4,6-triiodoisophthalamide is presented (Scheme 2).

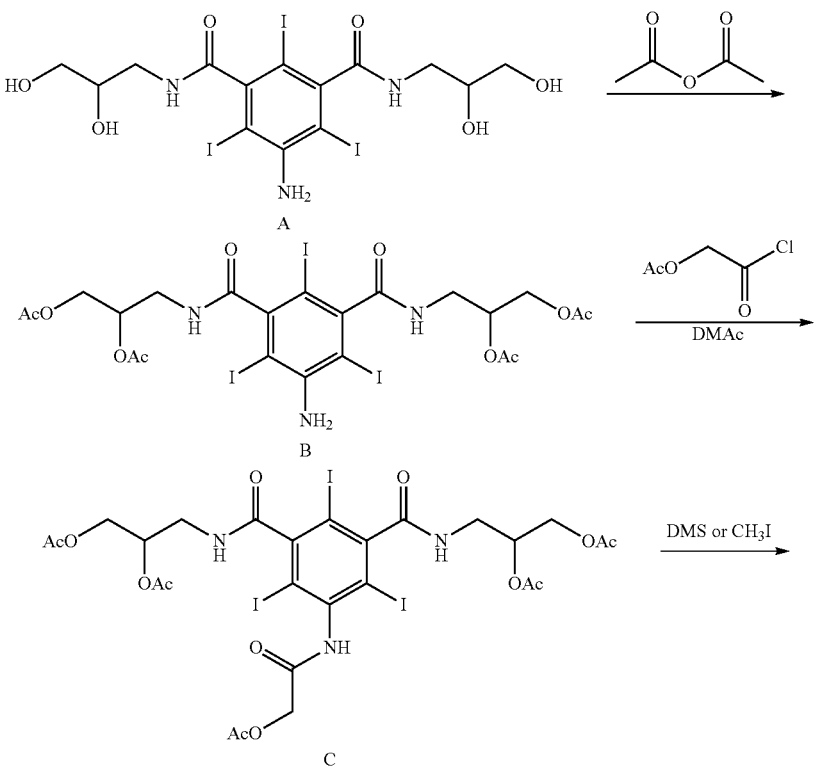

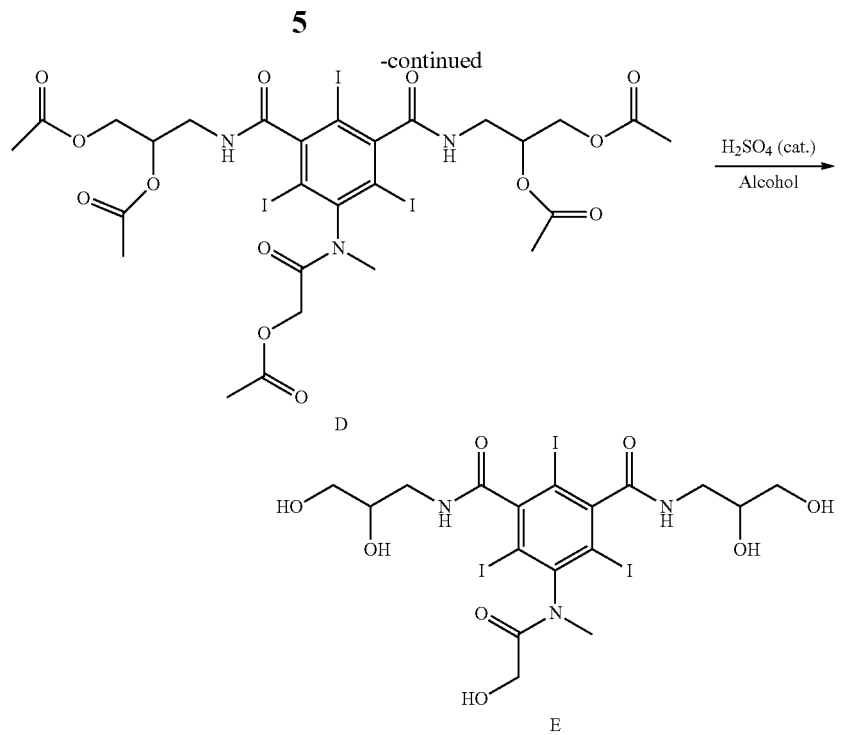

Although the above manufacturing method has the advantage of removing inorganic substances in the extraction process by using a new oil-soluble intermediate, it has the disadvantage that the manufacturing time is long due to the manufacturing process consisting of 4 steps, which increases the manufacturing cost in actual production.

Therefore, in order to compensate for the disadvantages of the above-described manufacturing processes, development of a manufacturing process that removes inorganic salts without using an ion exchange resin and a manufacturing technology capable of securing economical efficiency by shortening the manufacturing time while minimizing reaction impurities is needed.

PRIOR ART PUBLICATION

Patent Publication (Patent Publication 1) WO0032561 A
(Patent Publication 2) WO8809328 A
(Patent Publication 3) Korean Patent No. 101833334 A

SUMMARY

Problems to be Solved

The purpose of the present invention is to provide a method for preparing an X-ray contrast agent iomeprol which is capable of minimizing impurities generated during the reaction and easily removes inorganic salts while significantly shortening the manufacturing time compared to the existing one by performing N-methylation reaction by adding an inorganic base, an inorganic chloride and a solvent that dissolves inorganic chloride to commercially available 5-(2-hydroxyacetamido)-N,N'-bis(2,3-dihydroxypropyl)-2,4,6-triiodoisophthalamide.

Technical Means

In order to achieve the technical purpose, in the first aspect, the present invention provides a novel method for preparing a contrast agent iomeprol represented by Formula 1a, comprising a step of performing N-methylation reaction quickly and stably by adding a N-methylating agent, an inorganic base, an inorganic chloride and a solvent that dissolves inorganic chloride, such as methanol, DMSO, DMAc and DMF, to 5-(2-hydroxyacetamido)-N,N'-bis(2,3-dihydroxypropyl)-2,4,6-triiodoisophthalamide of Formula 1b.

Effect of the Invention

The method for preparing iomeprol according to the present invention can shorten the manufacturing time, minimize impurities generated during the reaction and obtain a high purity iomeprol of 99% or more due to allowing the inorganic chloride to be dissolved in the reaction solvent and the crystallization solvent while effectively separating and removing the inorganic salt without using a separate ion exchange resin by performing N-methylation reaction at a specific temperature by adding an N-methylating agent, an inorganic base, an inorganic chloride and a solvent that dissolves inorganic chloride to 5-(2-hydroxyacetamido)-N,N'-bis(2,3-dihydroxypropyl)-2,4,6-triiodoisophthalamide (Formula 1b).

DETAILED DESCRIPTION

The present invention is explained in more detail below.

The method for preparing iomeprol of the present invention comprises a step of performing N-methylation reaction by adding an N-methylating agent, an inorganic base, an inorganic chloride and a solvent to 5-(2-hydroxyacetamido)-N,N'-bis(2,3-dihydroxypropyl)-2,4,6-triiodoisophthalamide (Formula 1b).

The preparing method of the present invention is specifically composed of a process as in Scheme 3 below.

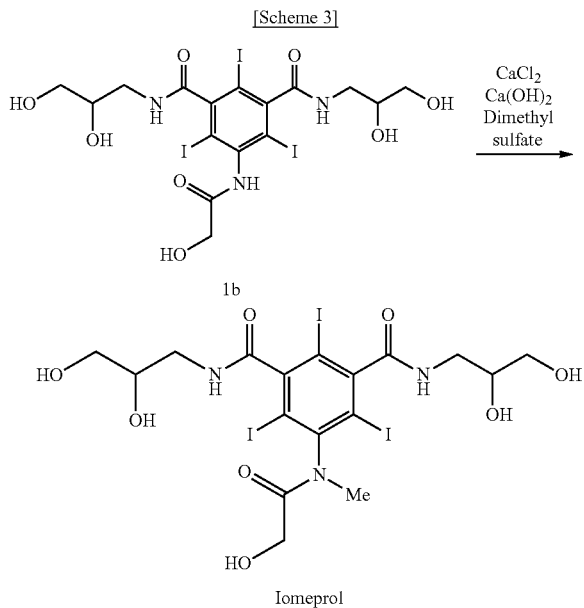

In the preparing method of the present invention, a contrast agent iomeprol (Formula 1a) is prepared by adding an N-methylating agent, an inorganic base, an inorganic chloride and a solvent that dissolves inorganic chloride to 5-(2-hydroxyacetamido)-N,N'-bis(2,3-dihydroxypropyl)-2,4,6-triiodoisophthalamide (Formula 1b).

In general, 5-(2-hydroxyacetamido)-N,N'-bis(2,3-dihydroxypropyl)-2,4,6-triiodoisophthalamide represented by Formula 1b has five alcohol groups, but it does not dissolve well in water or alcohol.

In order to perform the N-methylation reaction, the compound of Formula 1b must first be dissolved. In order to proceed with this, an inorganic chloride—i.e., calcium chloride—is added to make an ionic bond with an alcohol group to make a condition for dissolving in water or methanol.

The inorganic base functions as a Brønsted base to remove the hydrogen from the amide group for N-methylation reaction.

Specifically, as shown in Scheme 4, after 5-(2-hydroxyacetamido)-N,N'-bis(2,3-dihydroxypropyl)-2,4,6-triiodoisophthalamide (Formula 1b) and inorganic chloride are added to a solvent such as dimethyl sulfoxide (DMSO) or methanol and stirred to dissolve, Brønsted base sodium hydroxide is added thereto and N-methylating agent dimethyl sulfate is dissolved in a reaction solvent.

The N-methylating agent used in the preparation method of the present invention is selected from the group consisting of dimethyl sulfate, methyl iodine and a combination thereof, and is preferably dimethyl sulfate.

In the preparation method of the present invention, 1 or more equivalents, preferably 3 to 4 equivalents of N-methylating agent are used based on 1 equivalent of 5-(2-hydroxyacetamido)-N, N'-bis(2,3-dihydroxypropyl)-2,4,6-triiodoisophthalamide.

If the content of the N-methylating agent is less than the above numerical range, the reaction may be insufficient and the reaction time may increase. If the content of the N-methylating agent is greater than the above numerical range, impurities may increase.

The inorganic base used in the preparation method of the present invention is selected from the group consisting of lithium hydroxide, calcium hydroxide, magnesium hydroxide, beryllium hydroxide and a combination thereof, and is preferably calcium hydroxide.

Inorganic bases such as calcium hydroxide generate inorganic salts such as calcium chloride and water after completion of the reaction, and the calcium chloride is well soluble in methanol as a reaction solvent and a later crystallization solvent, so that inorganic salts can be effectively removed without using an ion exchange resin. As a result, high purity iomeprol (Formula 1a) can be obtained.

In the preparation method of the present invention, 0.5 to 2 equivalents, preferably 0.6 to 1.2 equivalents, more preferably 0.6 to 0.7 equivalents of inorganic base may be used based on 1 equivalent of 5-(2-hydroxyacetamido)-N,N'-bis(2,3-dihydroxypropyl)-2,4,6-triiodoisophthalamide (Formula 1b).

If the content of the inorganic base is less than the above numerical range, there may be a problem with the reaction rate. If the content is greater than the above numerical range, there may be a problem of increasing impurities.

As the inorganic chloride used in the preparing method of the present invention, calcium chloride, lithium chloride, beryllium chloride, magnesium chloride, etc. which can be dissolved in methanol as a reaction solvent may be used.

In the case of preparing iomeprol without adding an inorganic chloride, the reactant 5-(2-hydroxyacetamido)-N,N'-bis(2,3-dihydroxypropyl)-2,4,6-triiodoisophthalamide (Formula 1b) is not dissolved in methanol, which is a reaction solvent. The reaction does not proceed easily, and even if some reactions proceed, the reaction may not be terminated and the reactant may remain.

Since the remaining reactant, the compound of Formula 1 b, has a structure similar to iomeprol, it is very difficult to remove the reactant after the reaction is completed.

In the preparing method of the present invention, 2 to 10 equivalents, preferably 2 to 4 equivalents, more preferably 3 equivalents of inorganic chloride may be used based on 1 equivalent of 5-(2-hydroxyacetamido)-N,N'-bis(2,3-dihydroxypropyl)-2,4,6-triiodoisophthalamide (Formula 1b).

If the content of the inorganic chloride is too much, the concentration of the reaction solution is high, so that dissolution or stirring may be difficult. If the content is too small or absent, the reaction may not be terminated because the compound of Formula 1b is not dissolved.

The solvent used in the preparing method of the present invention may be selected from the group consisting of methanol, dimethylformamide (DMF), dimethylacetamide (DMAc), dimethyl sulfoxide (DMSO) and a combination thereof. Preferably, methanol can be used.

In the preparing method of the present invention, the weight ratio of the solvent to 5-(2-hydroxyacetamido)-N,N'-bis(2,3-dihydroxypropyl)-2,4,6-triiodoisophthalamide (Formula 1b) may be 4 to 10 times, preferably 5 to 7 times.

If the content of the solvent is less than the above numerical range, dissolution may be difficult. If the content is greater than the above numerical range, additional effects such as yield cannot be obtained in the crystallization step.

The preparing method of the present invention further comprises a step of crystallizing the product by adding a crystallization solvent to the product obtained from the N-methylation reaction.

The crystallization solvent may be any one selected from the group consisting of methanol, ethanol, isopropanol, normal butanol, 2-butanol or a combination thereof, preferably methanol.

The crystallization solvent is for effectively removing the inorganic salt and increasing the yield.

In the crystallization step, after completion of the N-methylation reaction, acid (HCl, etc.) is added to acidify, and then a crystallization solvent is added to reflux and stir at room temperature to 80° C., preferably 70 to 80° C., for 2 to 24 hours, preferably 3 hours.

After that, the crystals are filtered, washed sufficiently with a crystallization solvent, and dried under reduced pressure at 50 to 90° C.

The present invention is explained in more detail through the following Examples and Comparative Examples. However, the scope of the present invention is not limited thereby in any manner.

EXAMPLES

Example 1

Preparation of Iomeprol 5 g (1 equivalent) of 5-(2-hydroxyacetamido)-N,N'-bis(2,3-dihydroxypropyl)-2,4,6-triiodoisophthalamide (Formula 1b) and 3.6 g (5 equivalents) of calcium chloride were added together to 25 g of methanol, and then dissolved by refluxing at room temperature or 70° C. for 60 minutes.

After cooling the temperature of the solution to 10 to 15° C., 0.3 g (0.62 equivalent) of calcium hydroxide was added, followed by stirring at the same temperature for 1 hour.

2.48 g (3 equivalents) of dimethyl sulfate was added to the reaction solution and stirred at the same temperature for 3 hours until the reaction was completed.

After completion of the reaction, 1 mL of HCl (35%) was added for acidification, and 25 mg of 2-butanol was added and stirred at a temperature of 70 to 80° C. for 2 hours. Then, the mixture was cooled, filtered and washed with 2-butanol to obtain a crude iomeprol.

After adding the above crude iomeprol to a mixture of 25 mL of methanol and 10 mL of water, the temperature was raised to 50° C. to dissolve them, then 20 mL of 2-butanol was added, and refluxed at 90° C. for 3 hours. Then, the mixture was cooled to room temperature to filter the resulting crystals.

After washing with 2-butanol, it was dried under reduced pressure at 90° C. for 12 hours to obtain 4.17 g of iomeprol (HPLC: 99.3%).

Example 2

Preparation of Iomeprol 5 g (1 equivalent) of 5-(2-hydroxyacetamido)-N,N'-bis(2,3-dihydroxypropyl)-2,4,6-triiodoisophthalamide (Formula 1b) and 3.6 g (5 equivalents) of calcium chloride were added together to 25 g of methanol, and then dissolved by refluxing at room temperature or 70° C. for 30 minutes.

After cooling the temperature of the solution to 0 to 5° C., 0.3 g (0.62 equivalent) of calcium hydroxide was added, followed by stirring at the same temperature for 1 hour.

2.48 g (3 equivalents) of dimethyl sulfate was added to the reaction solution and stirred at the same temperature for 7 hours until the reaction was completed.

After completion of the reaction, 1 mL of HCl (35%) was added for acidification, and 25 mg of 2-butanol was added and stirred at a temperature of 70 to 80° C. for 2 hours. Then, the mixture was cooled, filtered and washed with 2-butanol to obtain a crude iomeprol.

After adding the above crude iomeprol to a mixture of 25 mL of methanol and 10 mL of water, the temperature was raised to 50° C. to dissolve them, then 20 mL of 2-butanol was added, and refluxed at 90° C. for 3 hours. Then, the mixture was cooled to room temperature to filter the resulting crystals.

After washing with 2-butanol, it was dried under reduced pressure at 90° C. for 12 hours to obtain 4.21 g of iomeprol (HPLC: 99.1%).

Comparative Example 1 (No Inorganic Chloride Added)

5-(2-hydroxyacetamido)-N, N'-bis(2,3-dihydroxypropyl)-2,4,6-triiodoisophthalamide (Formula 1b) was added to 25 g of methanol, and then refluxed for 30 minutes.

After cooling the temperature of the turbid solution to 10 to 15° C., 0.3 g (0.62 equivalent) of calcium hydroxide was added, followed by stirring at the same temperature for 1 hour.

2.48 g (3 equivalents) of dimethyl sulfate was added to the reaction solution and stirred at the same temperature for 5 hours.

As a result of reactivity review by HPLC, the synthesis of iomeprol proceeded by 5%, and it was found that the reactivity was very low because more than 90% of 5-(2-hydroxyacetamido)-N, N'-bis(2,3-dihydroxypropyl)-2,4,6-triiodoisophthalamide (Formula 1b) remained.

Comparative Example 2 (No Inorganic Base Added)

5-(2-hydroxyacetamido)-N,N'-bis(2,3-dihydroxypropyl)-2,4,6-triiodoisophthalamide (Formula 1 b) and 3.6 g (5 equivalent) of calcium chloride were added together to 25 g of methanol, and then refluxed for 30 minutes.

After cooling the temperature of the solution to 10 to 15° C., 2.48 g (3 equivalents) of dimethyl sulfate was added to the reaction solution and stirred at the same temperature for 5 hours.

As a result of reactivity review by HPLC, the synthesis of iomeprol proceeded by 0.5%, and it was found that the reactivity was very low because more than 99% of 5-(2-hydroxyacetamido)-N,N'-bis(2,3-dihydroxypropyl)-2,4,6-triiodoisophthalamide (Formula 1b) remained.

As described above, since the present invention prepares a compound of Formula 1a by methylating compound of Formula 1b without additional intermediate steps by using inorganic bases, inorganic chlorides and a solvent that dissolves inorganic chlorides, the present invention can reduce the existing manufacturing process and time and prepare iomeprol of high purity without the need for a purification process by a separate ion exchange resin device.

The detailed description of the present invention is merely illustrative of the present invention, and is used only for the purpose of describing the present invention, but not for limiting the meaning or limiting the scope of the present invention described in the claims.

Therefore, those of ordinary skill in the art would understand that various modifications and other equivalent embodiments are possible therefrom.

Therefore, the true technical protection scope of the present invention should be determined by the scope of the appended claims.

What is claimed is:

1. Method for preparing iomeprol, comprising a step of performing an N-methylation reaction by adding an N-methylating agent, an inorganic base, an inorganic chloride and a solvent to 5-(2-hydroxyacetamido)-N,N'-bis(2,3-dihydroxypropyl)-2,4,6-triiodoisophthalamide.

2. The method for preparing iomeprol according to claim 1, wherein the N-methylating agent is any one selected from the group consisting of dimethyl sulfate, methyliodine and a combination thereof.

3. The method for preparing iomeprol according to claim 1, wherein 1 to 10 equivalents of N-methylating agent are used based on 1 equivalent of 5-(2-hydroxyacetamido)-N,N'-bis(2,3-dihydroxypropyl)-2,4,6-triiodoisophthalamide.

4. The method for preparing iomeprol according to claim 1, wherein the inorganic base is any one selected from the group consisting of lithium hydroxide, calcium hydroxide, magnesium hydroxide, beryllium hydroxide and a combination thereof.

5. The method for preparing iomeprol according to claim 1, wherein 1 to 10 equivalents of inorganic base are used based on 1 equivalent of 5-(2-hydroxyacetamido)-N,N'-bis(2,3-dihydroxypropyl)-2,4,6-triiodoisophthalamide.

6. The method for preparing iomeprol according to claim 1, wherein the inorganic chloride is any one selected from calcium chloride, lithium chloride, beryllium chloride and magnesium chloride.

7. The method for preparing iomeprol according to claim 1, wherein 2 to 10 equivalents of inorganic chloride are used based on 1 equivalent of 5-(2-hydroxyacetamido)-N,N'-bis(2,3-dihydroxypropyl)-2,4,6-triiodoisophthalamide.

8. The method for preparing iomeprol according to claim 1, wherein the solvent is any one selected from the group consisting of dimethylformamide (DMF), dimethylacetamide (DMAc), dimethyl sulfoxide (DMSO), methanol and a combination thereof.

9. The method for preparing iomeprol according to claim 1, wherein the weight ratio of the solvent to 5-(2-hydroxyacetamido)-N,N'-bis(2,3-dihydroxypropyl)-2,4,6-triiodoisophthalamide is from 4:1 to 10:1.

10. The method for preparing iomeprol according to claim 1, further comprising a step of crystallizing the product by adding a crystallization solvent to the product obtained from N-methylation reaction.

11. The method for preparing iomeprol according to claim 10, wherein the crystallization solvent is any one selected from the group consisting of methanol, ethanol, isopropanol, 1-butanol, 2-butanol and a combination thereof.

* * * * *